United States Patent
Schwartz et al.

[11] Patent Number: 5,282,823
[45] Date of Patent: Feb. 1, 1994

[54] INTRAVASCULAR RADIALLY EXPANDABLE STENT

[75] Inventors: Robert S. Schwartz; John Bresnahan, both of Rochester; Rebecca M. Bergman, North Oaks; Arthur J. Coury, St. Paul; Elaine Lindell, Blaine; Vincent W. Hull, Fridley, all of Minn.

[73] Assignee: Medtronic, Inc., Minneapolis, Minn.

[21] Appl. No.: 853,682

[22] Filed: Mar. 19, 1992

[51] Int. Cl.$^5$ .......................................... A61M 29/00
[52] U.S. Cl. ................... 606/198; 604/890.1; 623/1
[58] Field of Search .............. 606/198; 604/890.1; 623/1

[56] References Cited

U.S. PATENT DOCUMENTS

| | | |
|---|---|---|
| Re. 31,618 | 7/1984 | Mano et al. . |
| 2,836,131 | 5/1958 | Tapp . |
| 3,105,492 | 10/1963 | Jeckel . |
| 3,272,204 | 9/1966 | Artandi et al. . |
| 3,562,820 | 2/1971 | Braun . |
| 4,164,045 | 8/1979 | Bokros et al. . |
| 4,300,244 | 11/1981 | Bokros . |
| 4,313,231 | 2/1982 | Koyamada . |
| 4,319,363 | 3/1982 | Ketharanatha . |
| 4,441,215 | 4/1984 | Kaster . |
| 4,503,569 | 3/1985 | Dotter . |
| 4,553,545 | 11/1985 | Maass et al. . |
| 4,560,374 | 12/1985 | Hammerslag . |
| 4,580,568 | 4/1986 | Gianturco . |
| 4,647,416 | 3/1987 | Seiler, Jr. . |
| 4,649,922 | 3/1987 | Wiktor . |
| 4,655,771 | 4/1987 | Wallsten . |
| 4,662,404 | 5/1987 | LeVeen et al. . |
| 4,665,918 | 5/1987 | Garza et al. . |
| 4,681,110 | 7/1987 | Wiktor . |
| 4,733,665 | 3/1988 | Palmaz . |
| 4,739,762 | 4/1988 | Palmaz . |
| 4,740,207 | 4/1988 | Kreamer . |
| 4,760,849 | 8/1988 | Kropf . |
| 4,768,507 | 9/1988 | Fischell et al. . |
| 4,771,773 | 9/1988 | Kropf . |
| 4,776,337 | 10/1988 | Palmaz . |
| 4,787,899 | 11/1988 | Lazarus . |
| 4,795,458 | 1/1989 | Regan . |
| 4,800,882 | 1/1989 | Gianturco . |
| 4,820,298 | 4/1989 | Leveen et al. . |
| 4,848,343 | 7/1989 | Wallsten et al. . |
| 4,872,874 | 10/1989 | Taheri . |
| 4,878,906 | 11/1989 | Lindemann . |
| 4,886,062 | 12/1989 | Wiktor ...................... 623/1 |
| 4,990,155 | 2/1991 | Wilkoff . |
| 5,015,253 | 5/1991 | MacGregor . |
| 5,019,085 | 5/1991 | Hillstead . |
| 5,019,090 | 5/1991 | Pinchuk . |
| 5,019,393 | 5/1991 | Ito et al. ................... 604/890.1 |
| 5,059,211 | 10/1991 | Stack et al. . |
| 5,061,275 | 10/1991 | Wallsten et al. . |
| 5,078,726 | 1/1992 | Kraemer . |
| 5,102,417 | 4/1992 | Palmaz ...................... 623/11 |
| 5,123,917 | 6/1992 | Lee . |

FOREIGN PATENT DOCUMENTS 0421729 10/1990 European Pat. Off. .
9112779 9/1991 World Int. Prop. O. .

OTHER PUBLICATIONS

WO 91/12779, Wolff, Rodney G., Intralumenal Drug Eluting Prosthesis, Sep. 5, 1991.

Primary Examiner—C. Fred Rosenbaum
Assistant Examiner—Noelle Kent Gring
Attorney, Agent, or Firm—Daniel W. Latham; Harold R. Patton

[57] ABSTRACT

A radially expandable stent for implantation within a body lumen having a generally cylindrical body with open proximal and distal ends, the cylindrical body comprising a plurality of metal elements joined to allow flexing of the cylindrical body along the longitudinal axis of the body whereby the stent can conform to a curved body lumen and a polymeric film extending between the metal elements of the stent. The stent provides a biocompatible polymeric surface to contact and support a body lumen and also a flexible structure to allow the stent to conform closely to bends in a body lumen. The stent is especially useful for repairing an injury to blood vessels caused during angioplasty procedures.

8 Claims, 4 Drawing Sheets

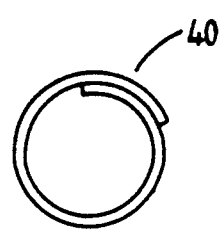
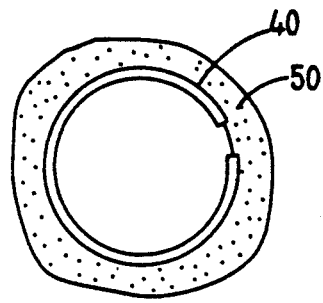
FIG. 12   FIG. 13
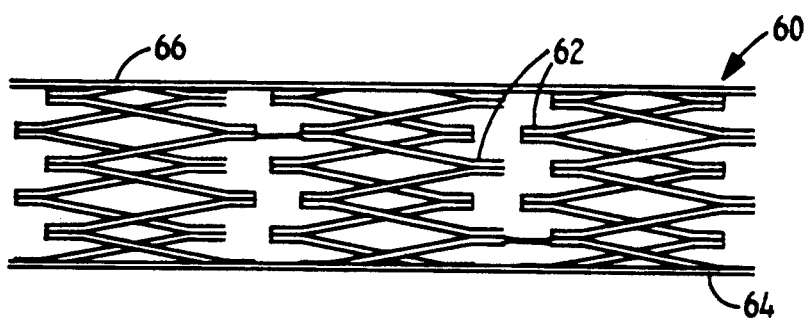
FIG. 14
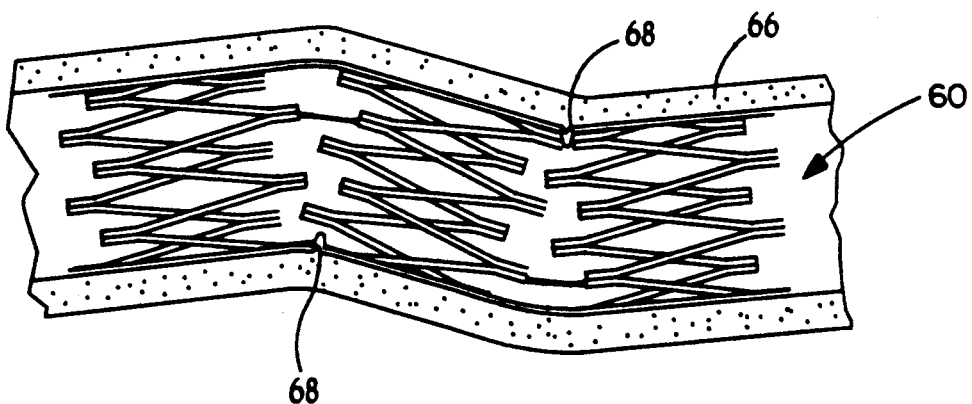
FIG. 15

INTRAVASCULAR RADIALLY EXPANDABLE STENT

BACKGROUND OF THE INVENTION

This invention relates to intraluminal stent implants for maintaining patency of a body lumen in humans and animals and especially to such implants for use in blood vessels. The present invention comprises an improvement to stents which are generally cylindrical in shape and have a plurality of metal elements joined to permit flexing of the cylindrical body along the longitudinal axis of the body whereby the stent can conform to a curved body lumen. One such stent has metal elements made up of wire loops in a wound structure which allows individual loops to move with respect to one another. When a stent with this structure is expanded in a body lumen, the winding can follow curves in the body lumen. Such a stent is disclosed in U.S. Pat. No. 4,886,062 issued to Wiktor which is incorporated herein by reference. Another such stent is a stent having metal elements made up of individual stent segments joined together by hinges such that the hinges will allow the stent segments to adapt to curved body lumen. Such a stent is disclosed in published European Patent Application 0421729 by Wolff which is incorporated herein by reference. These stents can be deployed in a body lumen by means appropriate to their design. For example, in the case of the Wiktor stent, it can be fitted over the inflatable element of a balloon catheter and expanded by the balloon to force the stent into contact with the body lumen. Or, for example, in the case of the Wolff stent, it can be mounted onto a catheter which holds the stent as it is delivered through the body lumen and then releases the stent and allows it to expand into contact with the body lumen. This deployment is effected after the stent has been introduced percutaneously, transported transluminally and positioned at a desired location by means of the catheter.

An important use of these metal stents is found in situations where part of the vessel wall or stenotic plaque blocks or occludes blood flow in the vessel. Dilation of the blood vessel is usually undertaken to correct a blood vessel occlusion i.e., a balloon catheter is utilized in a PTCA procedure to enlarge the occluded portion of the blood vessel. However, the dilation of the occlusion can form flaps, fissures and dissections which threaten re-closure of the dilated vessel or even perforations in the vessel wall. Implantation of a metal stent can provide support for such flaps and dissections and thereby prevent reclosure of the vessel or provide a patch repair for a perforated vessel wall until corrective surgery can be performed. Moreover, such metal stents with good longitudinal flexibility can conform readily to vessels having curves and irregularities. However, such stents have limited ability to provide effective patching of perforated vessels due to the spacing between metal elements. Also, such metal stents also have limited ability to carry and deliver drugs, such as anti-restenosis drugs or anti-coagulant drugs, to the site of an intravascular injury.

In U.S. Pat. No. 4,878,906 issued to Lindeman et al., an endoprosthesis made of a thin wall molded plastic sleeve is disclosed, the sleeve is intended to be collapsed radially and delivered to a damaged area of a vessel where it is expanded to provide a sealed interface to the vessel on its outer peripheral ends. The endoprosthesis therefore provides a patch which prevents leakage of blood from a vessel wall. The endoprosthesis disclosed employs various molded-in ribs, struts and the like to adapt the device for particular applications and to provide the desired degree of stiffness to form the sealed interface with the vessel wall. However, such a stiff prosthesis could not be expected to have the longitudinal flexibility needed to adapt to curved vessels.

Polymeric stents which can also provide therapeutic substances to the vessel wall have also been proposed such as in published International Patent Application WO 91/12779 "Intraluminal Drug Eluting Prosthesis" In that application, it is suggested that antiplatelet agents, anticoagulant agents, antimicrobial agents, antimetabolic agents and other drugs could be supplied in polymeric stents to reduce the incidence of restenosis.

It is therefore an object of the present invention to provide a stent having longitudinal flexibility which allows it to conform to curves and variations in body lumens.

It is also an object of the present invention to provide a stent capable of patching leaking blood vessels.

It is also an object of the present invention to provide a stent capable of delivering therapeutic agents to a blood vessel.

SUMMARY OF THE INVENTION

These and other objects have been accomplished by the stent of the present invention. In a radially expandable stent for implantation within a body lumen, the stent having a generally cylindrical body with open proximal and distal ends, the cylindrical body comprising a plurality of metal elements joined to permit flexing of the cylindrical body along its longitudinal axis to permit the stent to conform to a curved body lumen, the improvement of the present invention comprises a polymeric film extending between the metal elements. In essence, this improvement makes it possible to provide a stent able to support body lumens and conform to curves or irregularities in body lumens. This invention can be particularly useful in coronary angioplasty procedures in order to secure flaps and dissections in place following angioplasty and to patch perforations in the vessel wall. The composite stent of the present invention can be delivered to the site of the occlusion by catheter and expanded conventionally, causing the film to expand or open radially along with the metallic elements of the stent and to be brought into contact with the body lumen. The polymeric film is flexible and preferably an elastic or stretchable film that is capable of conforming to the movements of the metallic stent elements when expanded into contact with a body lumen. The film may also comprise strain relief to reduce the resistance of deformation for the stent such as by cuts, gaps or folds in the film between or on the metallic elements to ensure that the ability of the metallic elements of the stent to expand into contact with the body lumen and to conform to curved body lumens is not impaired. Since the stent of the present invention has a polymeric surface in contact with the body lumen, the stent can also incorporate therapeutic substances in or on the polymeric film such as those disclosed in published International Patent Application WO 91/12779 "Intraluminal Drug Eluting Prosthesis", which is incorporated herein by reference. The stent can then be used to administer such therapeutic substances to the vessel and to the bloodstream for the prevention of thrombosis or prevention of restenosis in the vessel.

BRIEF DESCRIPTION OF THE DRAWINGS

FIG. 12 is an end elevational view of the metal stent wire and film of FIG. 11 formed into a stent.

FIG. 13 is an end elevational view of the stent of FIG. 12 expanded into contact with a body lumen.

FIG. 14 is a side elevational view showing a stent with a polymeric film around the stent (shown in cross section).

FIG. 15 is a side elevational view of the stent and polymeric film of FIG. 14.

DETAILED DESCRIPTION OF THE INVENTION

Figure 1:
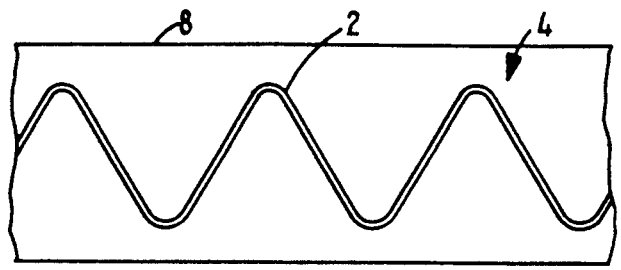
FIG. 1 is a plan view of a metal stent wire incorporated in a polymeric film.

The present invention relates to a radially expandable stent for implantation within a body lumen, the stent having a generally cylindrical body with open proximal and distal ends, the cylindrical body comprising a plurality of metal elements joined to permit flexing of the cylindrical body along its longitudinal axis to permit the stent to conform to a curved body lumen. A stent of this type is described, for example, in U.S. Pat. No. 4,886,062 issued to Wiktor which is incorporated herein by reference.

The improvement of the present invention includes applying to the above-mentioned type of stent a flexible or elastomeric polymeric film which extends between the metal elements. This improvement makes it possible to provide a stent suitable for supporting and patching body lumens while retaining the metal stents capability to conform to curved or irregular body lumens. Further, since the stent of the present invention has a polymeric surface in contact with the body lumen, the stent may also incorporate therapeutic substances in or on the polymeric film such as those disclosed in published International Patent Application WO 91/12779 "Intraluminal Drug Eluting Prosthesis", which is incorporated herein by reference. The stent can then be used to administer such therapeutic substances to the vessel and to the bloodstream for the prevention of thrombosis or prevention of restenosis in the vessel.

Therefore, a stent configuration of this invention is shown in FIGS. 1–9. A wire 2 (having a preferred diameter in the range of about 0.005 inch to 0.010 inch) is initially preformed into a two-dimensional zig-zag form, basically creating a flat expandable band 4. The zig-zag pattern can vary as to its shape and the tightness of the reversing bends. The flat expandable band 4 can then be provided with a flexible polymeric film 8. The film 8 can be made from virtually any type of biostable or biodegradable polymer which is suitable for implantation in a human or animal body. For example, the polymer can be a polyurethane, a polyester, polylactic acid, a polyamino acid, polyorthoester, polyphosphate ester or composites thereof. The term "film" or "flexible film" herein therefore means that, as applied to the metal stent elements in a thin cross section, the film is capable of flexing or stretching to preserve the radial expandability and axial flexibility of the implanted stent. The film 8 is preferably made from a highly elastic or stretchable material in order to allow the metal elements of the stent to flex easily. For example, a polyurethane film 8 can be applied to the flat expandable band 4 from a polyurethane solution. A solution of polyurethane (e.g. a 3% solids solution of polyurethane in methyl-2-pyrrolidone) is poured in a very thin coat into a suitable cylindrical mold. Preferably the urethane is a biostable urethane such as that disclosed in U.S. Pat. No. 4,873,308 issued to Coury et al. which is incorporated herein by reference. The flat expandable band 2 is than placed into the petri dish in contact with the polyurethane solution and the petri dish with flat expandable band are placed into an oven for a short period (e.g. one hour at 90° C.). The petri dish is then removed from the oven and additional polyurethane solution is added over the expandable band. The petri dish is then returned to the oven until the solvent is substantially removed from the polyurethane. The resulting flat expandable band 4 with flexible film 8 is then removed from the petri dish and the excess film is trimmed off with a sharp knife. The resulting film can be less than about 0.005 inch thick and also encloses the metal of the expandable band 4.

Figure 2:
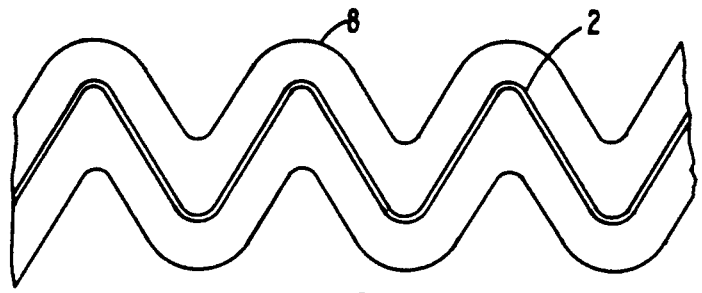
FIG. 2 is a plan view of the metal stent wire and film of FIG. 1 in which a portion of the film has been removed in order to conform it to the contours of the stent wire.
Figure 3:
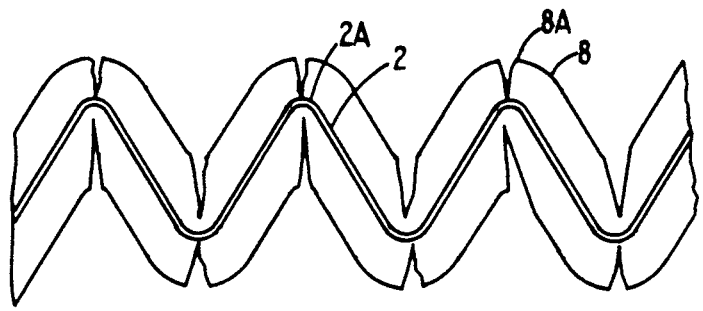
FIG. 3 is a plan view of the metal stent wire and film of FIG. 2 in which a further portion of the film has been removed.

The film 8 then may be trimmed as indicated in FIG. 2 to match the zig-zag contour of the wire 2. Since radial expansion of the stent may cause elastic or plastic deformation of the film 8 as set forth in FIG. 2 which may provide resistance to the expansion of the stent, the film may also be cut to provide strain relief at major bend points. In FIG. 3, the film 8 has been cut at major bend points 2A of the wire 2 from an outer edge of the film 8A to the wire 2. The shape of the cut is not critical. It can be a slit or a v-shaped cut with the removal of film material as shown.

Figure 4:
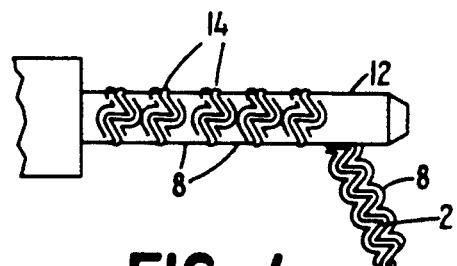
FIG. 4 is an elevation showing metal stent elements according to the present invention being formed by winding the stent wire and film of FIG. 3 on a mandrel.

In order to create a stent and to have it assume an initial configuration as shown in FIG. 4, a length of preformed band 4 with flexible film 8 is wrapped or coiled on a suitable mandrel 12 in a manner similar to that of winding a simple helical spring. Care is taken to form the band 4 and film 8 flat around the mandrel 12 with little or no tension to prevent premature linear expansion of the band 4 or tearing of the film 8. This produces a stent having a cylindrical body with a plurality of metal elements consisting of individual windings 14 joined in a helical configuration to permit flexing of the cylindrical body along its longitudinal axis. This will permit the stent to conform to a curved or irregularly-shaped body lumen. It also produces a stent having a flexible film 8 which extends between the metal elements of the stent and which will not significantly affect the ability of the stent to conform to curved body lumens. As shown, the film 8 need not join the individual windings 14 of the stent. Also, overlap of the film 8 on adjacent windings 14 is not required in the present invention although it will be appreciated by those skilled in the art that overlap can be provided, if desired, by trimming the film 8 wider or reducing the intervals between individual windings 14. It will also be appreciated by those skilled in the art that the discontinuity of the film 8 between adjacent windings 14 provides means for relieving longitudinal strain on the stent as it is expanded in a body lumen. It is therefore free to move with the portion of the winding to which it is attached to allow the stent to conform readily to curved or irregular-shaped body lumens. In other stent designs, strain relief can be provided by cutting or folding the film or by providing a high degree of elasticity or stretchability in the polymeric material used for the film and by maintaining very thin film cross sections (e.g. a film thickness of preferably as little as 0.001 inch, but more typically in the range of 0.002 to 0.010 inch and preferably about 0.003 to 0.005 inch). This structure may be radially expanded in a body lumen by the use of a balloon or other expansion device.

Figure 5:
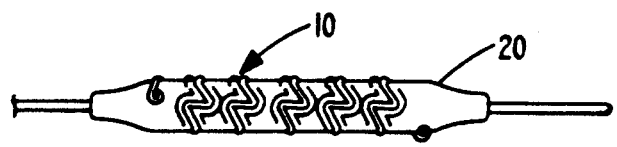
FIG. 5 is an elevation showing an overall view of the wound metal stent elements and incorporated polymeric film fitted over a deflated balloon.

Referring now to FIG. 5, once the zig-zag band 4 and flexible film 8 is wound into a coiled cylindrical shape to form a stent 10, it is removed from the mandrel 12, and is placed over a suitable expandable diameter device such as an inflatable balloon 20 typically used for angioplasty procedures. This is shown in FIG. 5. A suitable crimping tool (not shown) may be used to tighten the stent 10 over the balloon. A manual operation of sequentially squeezing the stent over the balloon is also acceptable.

Controlled radial expansion of the stent 10 is accomplished by the force generated in inflating the balloon 20. When acted upon by the inflating balloon 20 the stent 10, being characterized by the zig-zag preformed wire band 4 and flexible film 8, is subsequently formed into an open-ended cylindrical shape. By design and intent it is capable of expanding radially.

The radial expansion in effect is achieved by controlled deformation and tension applied to the sinusoidal pattern of the preformed wire band 4 with minimal resistance from the flexible film 8. The low memory metal used for the fabrication of the wire formed stent and flexibility of the film assures that the radially expanded stent stays expanded thus fulfilling its primary intent and function to provide support in a body lumen such as a blood vessel for any flaps or dissections in the lumen wall.

It will be appreciated by those skilled in the art that a polymeric film can be applied to the windings of the stent by other means than those described above. For example, a preformed film for the desired thickness can be applied to the stent windings by wrapping a sheath of the film material around the stent windings or by winding the film around the windings. In the case of a relatively inelastic film material, the flexible film can be provided with folds or pleats when attached to the stent in order to provide the necessary flexibility and expandability. Mechanical or adhesive attachment methods can be used to attach the film to the windings.

For purposes of better understanding this invention detailed reference is made to FIGS. 1-9. The embodiment of this invention is shown and described in an application for angioplasty; however, it is understood that other applications not specifically mentioned herein are possible and no limitations in scope of this invention are intended or implied.

The wire 2 used for the stent winding and elongated lead may be made of drawn low-memory level material such as tantalum, stainless steel, titanium ASTM F63-83 Grade 1 or high carat gold K 19-22. Titanium and gold are biologically compatible and inert and require no special treatment. Tantalum is the preferred stent material.

Figure 6:
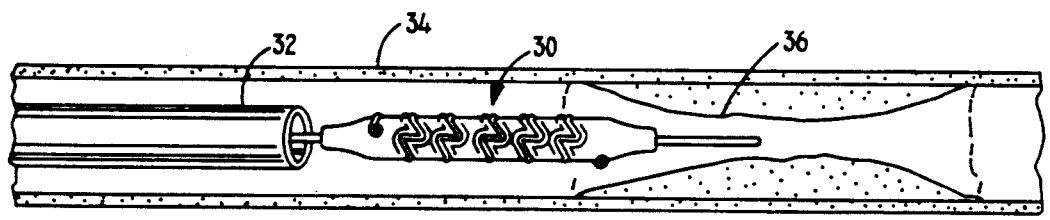
FIG. 6 shows the balloon and stent assembly of FIG. 5 advanced within a vessel, approaching a partial occlusion.
Figure 7:
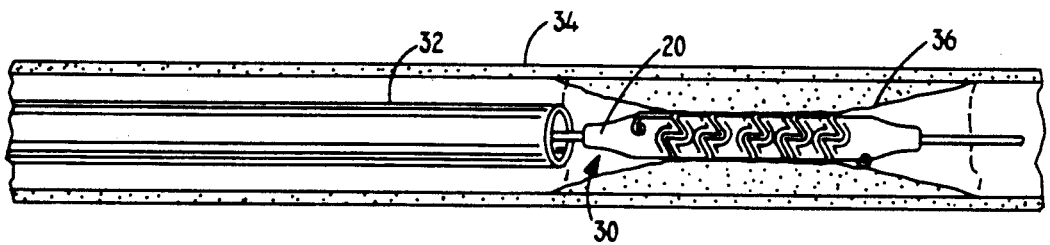
FIG. 7 is similar to FIG. 6 showing the balloon and stent assembly inside a partially occluded vessel.
Figure 8:
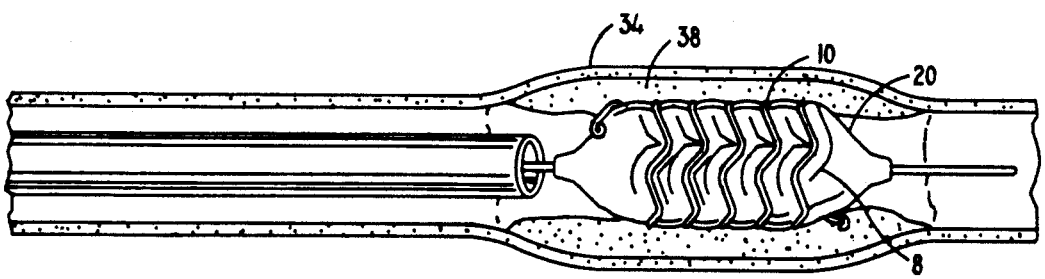
FIG. 8 is similar to FIG. 7 showing the balloon being inflated and the stent being radially expanded, illustrating an angioplasty procedure coupled with a simultaneous deployment and implantation of a stent of the present invention.
Figure 9:
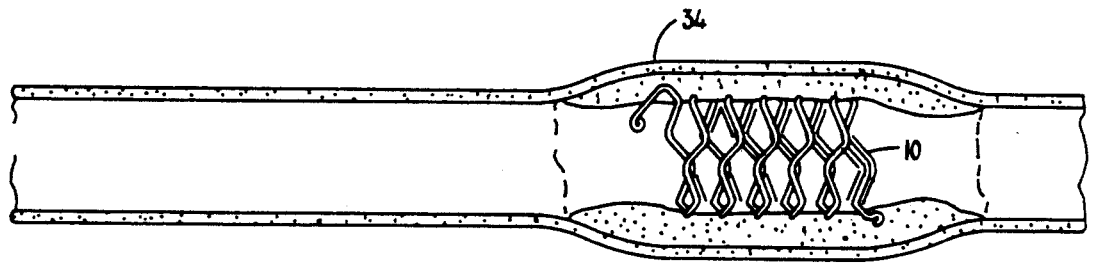
FIG. 9 is a view similar to FIG. 8 showing the prosthesis stent implanted with the polymeric film retained at the vessel wall after removal of the balloon.
Figure 10:
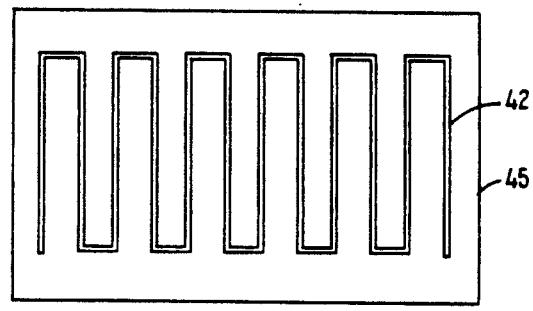
FIG. 10 is a plan view of a metal stent wire incorporated in a polymeric film.
Figure 11:
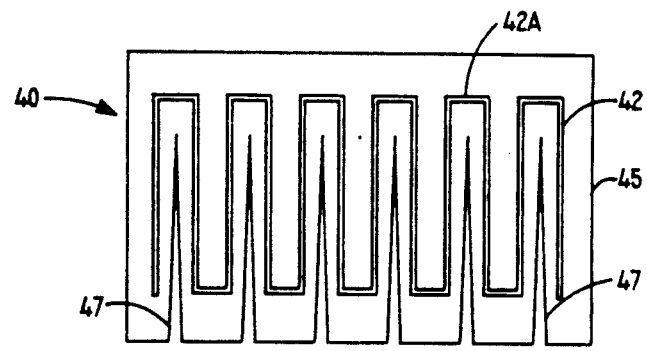
FIG. 11 is a plan view of the metal stent wire and film of FIG. 10 in which a portion of the film has been removed.

In FIG. 6 it is seen how balloon and stent assembly 30 with incorporated flexible film 8 emanate from guiding catheter 32 inside vessel 34 and are advanced towards partial occlusion 36. It will be appreciated by those skilled in the art that although the balloon and stent assembly 30 is shown with an undilated occlusion 36, the stent of the present invention can also be used in predilated vessels in order to support flaps or dissections caused by the dilation procedure. In FIG. 7 it is seen how balloon and stent assembly 30 are located in occlusion 36 within artery 34, balloon 20 still being deflated. Once positively placed, such as within occlusion 36, balloon 20 is inflated using standard angioplasty procedures and techniques. As balloon 20 expands, so does stent 10 as shown in FIG. 8 together with flexible film 8. The expanding balloon 20 together with stent 10 contacts the plaque 38 and expands the vessel 34. As shown in FIG. 9, with the angioplasty procedure completed, balloon is deflated and withdrawn leaving stent 10 firmly implanted within vessel 34 with film held in contact with the vessel 34. Previously occluded vessel 34 is now supported by stent 10 and patency is restored.

Referring now to FIGS. 10 to 13, another stent 40 according to the present invention is depicted. A zig-zag stent wire 42 is formed and a polymeric film 45 is formed on the wire 42 by application of a urethane in a solvent as set forth above. In order to provide additional strain relief so that the stent 40 can more readily conform to curves and irregularities in a body lumen as it is expanded, the film 45 is provided with incut portions 47 extending between the zigzags 42A in the wire 42. The stent 40 is then rolled into a cylindrical configuration suitable for delivery into a body lumen. As shown in FIG. 13, the stent 40 can be delivered to the body lumen 50 and expanded (e.g. by use of a balloon catheter) into contact with the body lumen 50.

Referring now to FIGS. 14 and 15, a self expanding stent 60 comprising joined metal stent elements 62 is shown. The joined metal stent elements 62 are as disclosed in published European Patent Application 0421729 by Wolff which is incorporated herein by reference. The stent 60 also comprises a flexible film 64. The flexible film 64 can be applied as a sheath to the metal stent elements 62 after which the stent 60 can be compressed, attached to a catheter, and delivered through a body lumen to a desired location. Once in the desired location, the stent 60 can be released from the catheter and expanded into contact with the lumen 66 as shown in FIG. 15 where it can conform to the curvature of the body lumen 66. The flexible film 64 is able to form folds 68 which allow the stent elements to readily adapt to the curvature of the body lumen 66.

In yet another aspect of the present invention, various therapeutic substances can be incorporated in or applied to the polymeric film to provide such substances to the blood or to the lumen wall. By "therapeutic substance" we mean to include drugs such as those described WO 91/12779 "Intraluminal Drug Eluting Prosthesis" which is incorporated herein by reference. In that application, it is suggested that antiplatelet agents, anticoagulant agents, antimicrobial agents, antimetabolic agents and other drugs could be supplied in polymeric stents to reduce the incidence of restenosis. We also mean to include within the scope of "therapeutic substance" any other material useful in diagnosis and treatment such as radio-opaque substances. Application of the therapeutic substance to the film can include applying it on the surface of the film or incorporating it into the film as it is made. For example, microcapsules can be used to carry the therapeutic substance either in or on the film and to provide timed-release of the substance to the blood or to the blood vessel or both. Microcapsules which are suitable for use in the present invention are well known. For example, the disclosures of U.S. Pat. Nos. 4,897,268; 4,675,189; 4,542,025; 4,530,840; 4,389,330; 4,622,244; 4,464,317; and 4,943,449 could be used and are incorporated herein by reference. Microcapsules containing one type of therapeutic substance could be provided on one side of the film and microcapsules containing another therapeutic substance could be incorporated on the other side of the film, thus providing a stent according to the present invention which provides one type of therapeutic substance (e.g. an antithrombotic drug) to the blood and another type of therapeutic substance (e.g. an antiproliferative drug) to the vessel wall. This can be accomplished, for example, with the solution-derived polyurethane film described above by first placing microcapsules containing the first therapeutic substance in a petri dish. A solution of polyurethane (e.g. a 3% solids solution of polyurethane according to U.S. Pat. No. 4,873,308 in methyl-2-pyrrolidone) is then poured over the microcapsules in the petri dish. A flat expandable band as described above is than placed into the petri dish in contact with the polyurethane solution and the petri dish with the band are placed into an oven for a short period. The petri dish is then removed from the oven and additional polyurethane solution is added over the expandable band and microcapsules containing a second therapeutic substance are then added to the additional polyurethane solution. The petri dish is then returned to the oven until the solvent is substantially removed from the polyurethane. The resulting flat expandable band with flexible film is then removed from the petri dish and the film and band are made into a stent as described above. The resulting stent has microcapsules containing one therapeutic substance on the inside (and able to contact blood once implanted in a blood vessel) and microcapsules containing a second therapeutic substance on the outside (and able to contact the vessel wall when implanted in contact with the vessel wall).

This completes the description of the preferred and alternate embodiments of the invention. Those skilled in the art may recognize other equivalents to the specific embodiment described herein which equivalents are intended to be encompassed by the claims attached hereto.

We claim:

1. In a radially expandable stent for implantation within a body lumen, the stent having a generally cylindrical body with open proximal and distal ends, the cylindrical body comprising a plurality of substantially helical metal elements joined to allow flexing of the stent along its longitudinal axis in a continuous, substantially helical wire winding, the improvement comprising:

a polymeric film extending between the helical metal elements of the stent wherein the polymeric film has strain relief means between the helical metal elements and wherein the strain relief means comprises one or more cuts in the film between adjacent helical metal elements.

2. The stent of claim 1 wherein the helical metal elements are also formed into a zig-zag.

3. The stent of claim 2 wherein the film extends helically along the helical metal elements.

4. The stent of claim 3 wherein the film is also provided with strain relief means between the zig-zags.

5. The stent of claim 4 wherein the strain relief means comprise cuts extending inwardly from the edge of the film to the helical metal elements.

6. The stent of claim 1 wherein the film has a thickness of less than about 0.010 inch.

7. The stent of claim 1 wherein the film also encloses the metal elements.

8. The stent of claim 1 wherein the film comprises a therapeutic substance.

* * * * *